(12) United States Patent
Cheng et al.

(10) Patent No.: US 9,873,719 B2
(45) Date of Patent: Jan. 23, 2018

(54) SALT AND PROTEASE-RESISTANCE OF ANTIMICROBIAL PEPTIDE AND THE MANUFACTURE THEREOF

(71) Applicant: National Tsing Hua University, Hsinchu (TW)

(72) Inventors: Jya-Wei Cheng, Hsinchu (TW); Hui-Yuan Yu, Hsinchu (TW); Hsi-Tsung Cheng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 14/273,064

(22) Filed: May 8, 2014

(65) Prior Publication Data
US 2015/0148285 A1 May 28, 2015

(30) Foreign Application Priority Data
Nov. 28, 2013 (TW) .............................. 102143445 A

(51) Int. Cl.
*C07K 7/08* (2006.01)
*C07K 7/06* (2006.01)
*C07K 5/11* (2006.01)

(52) U.S. Cl.
CPC .............. *C07K 7/08* (2013.01); *C07K 5/1019* (2013.01); *C07K 7/06* (2013.01)

(58) Field of Classification Search
CPC ........... C07K 5/1019; C07K 7/06; C07K 7/08
See application file for complete search history.

(56) References Cited

U.S. PATENT DOCUMENTS

| 5,382,569 A * | 1/1995 | Cody et al. ..................... 514/1.7 |
| 7,232,803 B2 * | 6/2007 | Svendsen et al. ............. 514/2.3 |
| 7,407,940 B2 * | 8/2008 | Falla ......................... C07K 7/06 514/2.3 |
| 7,414,029 B2 * | 8/2008 | Peri ........................... C07K 7/06 514/1.1 |
| 7,449,544 B2 * | 11/2008 | Zheleva ............. C07K 14/4738 530/317 |
| 9,073,967 B2 * | 7/2015 | Cheng ...................... C07K 7/08 |
| 2003/0195144 A1 * | 10/2003 | Svendsen ............... A61K 38/08 514/2.3 |
| 2006/0128614 A1 * | 6/2006 | Cheng .................. C07K 5/1019 514/2.1 |
| 2013/0109834 A1 * | 5/2013 | Cheng et al. ................. 530/327 |

FOREIGN PATENT DOCUMENTS

WO   WO2004/094462   *   4/2004

OTHER PUBLICATIONS

Paradis-Bas et al. Linear versus branched poly-lysine/arginine as polarity enhancer tags. Organic and Biomolecular Chemistry, 2014, 12, pp. 7194-7196.*
Yu et al. Easy Strategy to Increase Salt Resistance of Antimicrobial Peptides. Antimicrobial Agents and Chemotherapy, 2011, pp. 4918-4921.*
Chu et al., "Boosting Salt Resistance of Short Antimicrobial Pepides", AAC Accepts, May 28, 2013, 13 pages.

* cited by examiner

*Primary Examiner* — Marcela M Cordero Garcia
(74) *Attorney, Agent, or Firm* — Muncy, Geissler, Olds & Lowe, P.C.

(57) ABSTRACT

An antimicrobial peptide has an amino terminal and/or carboxyl terminal linked with at least one artificial bulky amino acid to increase the salt resistance and protease resistance of the antimicrobial peptide. The antimicrobial peptide of the invention has a high salt resistance, a high protease resistance, and a low hemolytic activity, simultaneously.

4 Claims, 6 Drawing Sheets

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: Synthesized Sequence

<400> SEQUENCE: 1

Lys Lys Trp Arg Lys Trp Leu Ala Lys Lys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthesized Sequence

<400> SEQUENCE: 2

Lys Trp Trp Lys
1

<210> SEQ ID NO 3
<211> LENGTH: 10
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (3)..(3)
<223> OTHER INFORMATION: Xaa is Nal (Naphthylalanine)
<220> FEATURE:
<221> NAME/KEY: misc_feature
```

```
<222> LOCATION: (6)..(6)
<223> OTHER INFORMATION: Xaa is Nal (Naphthylalanine)

<400> SEQUENCE: 3

Lys Lys Xaa Arg Lys Xaa Leu Ala Lys Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (11)..(11)
<223> OTHER INFORMATION: Xaa is Nal (Naphthylalanine)

<400> SEQUENCE: 4

Lys Lys Trp Arg Lys Trp Leu Ala Lys Lys Xaa
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (11)..(12)
<223> OTHER INFORMATION: Xaa is Nal (Naphthylalanine)

<400> SEQUENCE: 5

Lys Lys Trp Arg Lys Trp Leu Ala Lys Lys Xaa Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (11)..(13)
<223> OTHER INFORMATION: Xaa is Nal (Naphthylalanine)

<400> SEQUENCE: 6

Lys Lys Trp Arg Lys Trp Leu Ala Lys Lys Xaa Xaa Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthesized Sequence

<400> SEQUENCE: 7

Lys Lys Trp Arg Lys Trp Leu Ala Lys Lys Trp
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthesized Sequence
```

```
<400> SEQUENCE: 8

Lys Lys Trp Arg Lys Trp Leu Ala Lys Lys Trp Trp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 9

Lys Lys Trp Arg Lys Trp Leu Ala Lys Lys Lys Lys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (5)..(5)
<223> OTHER INFORMATION: Xaa is Nal (Naphthylalanine)

<400> SEQUENCE: 10

Lys Trp Trp Lys Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (6)..(6)
<223> OTHER INFORMATION: Xaa is Nal (Naphthylalanine)

<400> SEQUENCE: 11

Lys Trp Trp Lys Phe Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (5)..(6)
<223> OTHER INFORMATION: Xaa is Nal (Naphthylalanine)

<400> SEQUENCE: 12

Lys Trp Trp Lys Xaa Xaa
1               5
```

SALT AND PROTEASE-RESISTANCE OF ANTIMICROBIAL PEPTIDE AND THE MANUFACTURE THEREOF

CROSS-REFERENCE TO RELATED APPLICATIONS

This Non-provisional application claims priority under 35 U.S.C. § 119(a) on Patent Application No(s). 102143445 filed in Taiwan, Republic of China Nov. 28, 2013, the entire contents of which are hereby incorporated by reference.

BACKGROUND OF THE INVENTION

Field of the Invention

The present invention relates to an antimicrobial peptide and the manufacture thereof, and in particular relates to an antimicrobial peptide with high salt resistance, low hemolytic activity, and high protease resistance formed by linking a bulky amino acid and the N-terminal or C-terminal of the antimicrobial peptide.

Description of the Related Art

Various bioactive peptides have been reported in both the scientific literature and in issued patents. Peptides historically have been isolated from natural sources, and have recently been the subject of structure-function relationship studies. Additionally, natural peptides have served as starting points for the design of synthetic peptide analogs.

A review of peptide antibiotics was published by R. E. W. Hancock in 1997 (*Lancet* 349: 418-422). The structure, function, and clinical applications of various classes of peptides were discussed. An additional review of cationic peptide antibiotics was published in 1998 (Hancock, R. E. W. and Lehrer, R. *Trends Biotechnol.* 16: 82-88). The peptides are typically cationic amphipathic molecules of 12 to 45 amino acids in length. The peptides permeabilize cell membranes leading to the control of microbial agents. The clinical potential of host defense cationic peptides was discussed by R. E. W. Hancock in 1999 (*Drugs* 57(4): 469-473; *Antimicrobial Agents and Chemotherapy* 43(6): 1317-1323). The antibacterial, antifungal, antiviral, anticancer, and wound healing properties of the class of peptides are discussed.

The protective function of antimicrobial peptides in innate host defense mechanisms has been demonstrated in *Drosophila*, where reduced expression of such peptides dramatically decreases survival rates after microbial challenge. In mammals, a similar function is suggested by defective bacterial killing in the lungs of cystic fibrosis patients and in small mice.

The antimicrobial peptides found in mammals may be classified into the cysteine-rich defensins (α- and β-defensin) and various groups within the cathelicidin family. Based on the amino acid composition and structure, the cathelicidin family may be classified into three groups. The first group includes the amphipathic α-helical peptides such as LL-37, CRAMP, SMAP-29, PMAP-37, BMAP-27, and BMAP-28. The second group contains the Arg/Pro-rich or Trp-rich peptides including Bac5, Bac7, PR-39, and indolicidin. The third group includes Cys-containing peptides such as protegrins.

It is believed that non-antibiotic antimicrobial drugs, such as antimicrobial peptide, may be a main scheme of development for anti-microorganism agents in the future. Since antibiotic resistance has become a major clinical and public health problem within the lifetime of most people living today, the non-antibiotic antimicrobial drugs will be have a wide of industrial application in the field of aquaculture and livestock. Therefore, non-antibiotic antimicrobial drugs may solve the problems raised by abuse of antibiotics.

Although salt-resistance antibacterial peptides were published, it has a high hemolysis when its salt-resistance is increased. Thus, an antimicrobial peptide with high salt resistance, low hemolytic activity, and high protease resistance is required.

BRIEF SUMMARY OF INVENTION

The antibacterial peptide is a biological macro-molecule, which is produced and secret by specific part of the organism. The physiological environment such as salt concentration, pH value, etc., is limited to certain degree, so as to limit the usage scope and effect. Therefore, moderate modifying the amino acids of this kind of peptide is helpful on medical field, applicable environmental field and general adaptive for development of formulation, so as to evaluate the therapeutic effect in high salt concentration environment. The present invention is related to developing a high-salt resistance antibacterial peptide and a method for increasing the salt resistance of antibacterial peptide, so as to solve the general problems in antibacterial peptides nowadays.

Accordingly, one aspect of the present invention is to provide an peptide represented by the formula (I): $A_n$-$(X_p)$-$B_m$, wherein $A_n$ and $B_m$ selected from a group consisting of bulky amino acid and β-Nal; p is from 1 to 9 ($1 \leq p \leq 9$); when n is 0, m is from 1 to 3 ($1 \leq m \leq 3$); and when m is 0, n is from 1 to 3 ($1 \leq n \leq 3$).

In one embodiment of the invention, the $(X_p)$ of the formula (I) comprises positive-charged amino acids or uncharged amino acids.

In one embodiment of the invention, the $(X_p)$ of the formula (I) comprises at least two positive-charged amino acids.

In one embodiment of the invention, the positive-charged amino acid is selected from a group consisting of lysine, arginine, and histidine.

In one embodiment of the invention, the uncharged amino acid is selected from a group consisting of leucine, isoleucine, alaine phenylalanine, glycine, serine, threonine, cysteine, tyrosine, asparagine, and tryptophan.

In one embodiment of the invention, the A or B is an artificial bulky amino acid.

In one embodiment of the invention, the A or B comprises β-Nal.

The invention also provides an artificial Xp, and its N-terminal or C-terminal has at least one artificial bulky amino acid.

In one embodiment of the invention, the molecule weight of the peptide is less than 1,000 kb.

In one embodiment of the invention, the peptide has 6-12 amino acids.

The invention further provides a method for increasing salt resistance and protease resistance of a peptide, comprising providing a peptide, and linking a bulkyl amino acid to the N-terminal and/or C-terminal of the peptide.

In one embodiment of the invention, the bulky amino acid comprises Bal, 1-Nal, β-naphthylalanine, Dip, Bip, Ath, or Tbt.

In one embodiment of the invention, the peptide is an antimicrobial peptide.

The invention also provides an antibiotic for suppressing microorganism infections, comprises a peptide of the invention and a pharmaceutically acceptable adjuvant or carrier.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

Figure 1A:
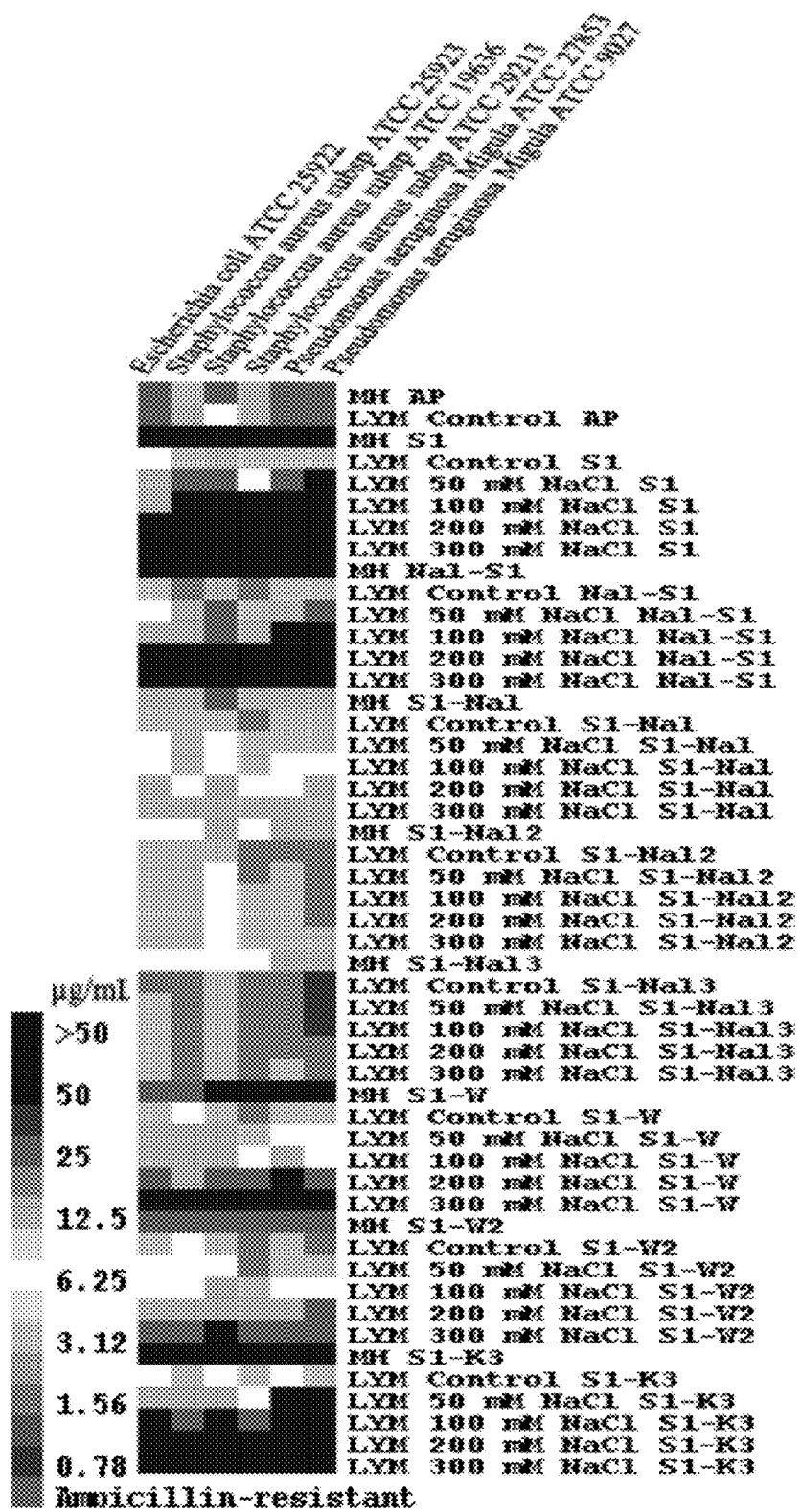
FIG. 1a shows the antimicrobial activity of the peptides.

The following description is of the best-contemplated mode of carrying out the invention. This description is made for the purpose of illustrating the general principles of the invention and should not be taken in a limiting sense. The scope of the invention is best determined by reference to the appended claims.

In one aspect of the invention, a short peptide represented by the formula (I): "$A_n$-$(X_p)$-$B_m$" is provided.

$(X_p)$ of the formula (I) refers to any short peptides. The length of the peptide is not limited. The peptide may have 1, 2, 3, 4, 5, 6, 7, 8, 9, 10, or more amino acids, preferably, from 1 to 9, more preferably, from 4 to 6.

$A_n$ and $B_m$ of the formula (I) may be the same or different. When n is 0, m is from 1 to 3 ($1 \leq m \leq 3$). When m is 0, n is from 1 to 3 ($1 \leq n \leq 3$).

In one embodiment, $(X_p)$ includes positive-charged or non-charged amino acids. In another embodiment, the number of positive-charged amino acids of $(X_p)$ is not limited, preferably, at least two positive-charged amino acids.

The positive-charged amino acids comprise lysine, arginine, and histidine, preferably, lysine.

The non-charged amino acids comprise leucine, isoleucine, alanine, phenylalanine, glycine, serine, threonine, cysteine, tyrosine, asparagine, and tryptophan, preferably, tryptophan.

$(X_p)$ of the formula (I) is a antimicrobial peptide, preferably.

The term "antimicrobial peptide" of the invention refers to any peptides with antimicrobial activity.

The term "antimicrobial activity" refers to the ability of a peptide of the present invention to modify a function or metabolic process of a target microorganism, for example so as to at least partially affect replication, vegetative growth, toxin production, survival, viability in a quiescent state, or other attribute. In an embodiment, the term relates to inhibition of growth of a microorganism. In a particular embodiment, antimicrobial activity relates to the ability of an inventive peptide to kill at least one bacterial species.

The term "microorganism" herein refers broadly to bacteria, fungi, viruses, and protozoa. In particular, the term is applicable for a microorganism having a cellular or structural component of a lipid bilayer membrane. In specific embodiments, the membrane is a cytoplasmic membrane. Pathogenic bacteria, fungi, viruses, and protozoa as known in the art are generally encompassed. Bacteria can include gram-negative and gram-positive bacteria in addition to organisms classified in orders of the class Mollicutes and the like, such as species of the *Mycoplasma* and *Acholeplasma* genera. Specific examples of potentially sensitive gram-negative bacteria include, but are not limited to, *Escherichia coli, Pseudomonas aeruginosa, Salmonella, Hemophilus influenza, Neisseria, Vibrio cholerae, Vibrio parahaemolyticus* and *Helicobacter pylori*. Examples of potentially sensitive gram-positive bacteria include, but are not limited to, *Staphylococcus aureus, Staphylococcus epidermis, Streptococcus agalactiae*, Group A *streptococcus, Streptococcus epidermis, Enterococcus faecalis*, Group B gram positive *streptococcus, Corynebacterium xerosis*, and *Listeria monocytogenes*. Examples of potentially sensitive fungi include yeasts such as *Candida albicans*. Examples of potentially sensitive viruses include measles virus, herpes, simplex virus (HSV-1 and -2), herpes family members (HIV, hepatitis C, vesicular, stomatitis virus (VSV), visna virus, and cytomegalovirus (CMV). Examples of potentially sensitive protozoa include *Giardia*.

The invention also provides an artificial short peptide, wherein the N-terminal or C-terminal of the peptide has at least one artificial bulky amino acid.

The artificial short peptide of the invention has a molecule weight of less than 1,000 kb. In one embodiment, the artificial short peptide of the invention has a length of 3-30 amino acids, preferably, 6-12 amino acids. Generally, the shorter peptide is more difficult to be metabolized and digested, and it is easier to be synthesized and has more economic benefits if the peptide is less than 12 amino acids. In another embodiment, the short peptide of the invention is an antimicrobial.

It shall be noted that the N-terminal or C-terminal of the artificial short peptide has at least one artificial bulky amino acid. The term "artificial bulky amino acid" of the invention includes, but is not limit to, Bal, 1-Nal, β-naphthylalanine (β-Nal), Dip, Bip, Ath, and Tbt, preferably, β-Nal.

The number of the artificial bulky amino acid is not limited, can be 1, 2, 3, 4, 5, 6, 7, 8, 9, or more, preferably, 1 to 3. Actually, the number of the artificial bulky amino acid can be changed depended on the length and molecular weight of the antimicrobial peptide. In one embodiment, although only one artificial bulky amino acid is linked, the salt-resistance of the peptides still can be increased.

The invention further provides an ultra short polypeptide. The ultra short polypeptide does not have an antimicrobial activity, inherently. When the N-terminal of the ultra short polypeptide is linked with one or more artificial bulky amino acid, the ultra short polypeptide would have a high salt resistance, a high protease resistance, and a low hemolytic activity, simultaneously.

The artificial bulky amino acid can increase the (1) antimicrobial activity, (2) salt-resistance, (3) stability (protease resistance) of the peptide, and (4) decrease the hemolytic activity of the peptide. Therefore, the antimicrobial peptides linked with the artificial bulky amino acids not only have high salt resistance, low hemolytic activity, high stability (high protease resistance), but also still retain or have a higher antimicrobial activity. Accordingly, the antimicrobial peptide of the invention has a high salt resistance, a high protease resistance, and a low hemolytic activity. The peptide of the invention has a wide application in various bio-organisms and tissue environment.

Unless artificial bulky amino acid, the peptide of the invention also can be linked with tryptophan or other amino acids or material, simultaneously.

Even if the artificial short peptide of the invention is placed in a high salt environment of more than 50 mM, 100 mM, or 150 mM, preferably, more than 200 mM, 250 mM, more preferably, more than 300 mM, the peptide of the invention still have an excellent antimicrobial activity. Additionally, the peptide of the invention have a protease resistance of more than 90%, preferably, 91%, 92%, 93%, 94%, 95%, 96%, 97%, 98%, 99%, or 100%. Meanwhile, the peptide of the invention has a hemolysis of less than 10%, preferably, less than 9%, 8%, 7%, 6%, 5%, 4%, 3%, 2%, or 1% at an effective antimicrobial concentration.

The invention further provides a method for increasing the salt-resistance and protease resistance of a peptide, comprising providing a peptide, and linking an artificial bulky amino acid (e.g., β-Nal) to the N-terminal or C-terminal of the peptide.

An embodiment of the invention is the use of the above described peptides to inhibit or kill microorganisms. The method generally is directed towards the contacting of microorganisms with the peptide. The contacting step can be performed in vivo, in vitro, topically, orally, transdermally, systemically, or by any other method known to those of skill in the art. The contacting step is preferably performed at a concentration sufficient to inhibit or kill the microorganisms. The concentration of the peptide can be at least about 0.1 μM, at least about 0.5 μM, at least about 1 μM, at least about 10 μM, at least about 20 μM, at least about 50 μM, or at least about 100 μM.

The contacting step can be performed by systemic injection, oral, subcutaneous, IP, IM, IV injection, or by topical application. For injection, the dosage can be between any of the following concentrations: about 1 mg/kg, about 5 mg/kg, about 10 mg/kg, about 25 mg/kg, about 50 mg/kg, about 75 mg/kg, and about 100 mg/kg. The contacting step can be performed on a mammal, a cat, a dog, a cow, a horse, a pig, a bird, a chicken, a plant, a fish, or a human.

EXAMPLE

Example 1: Preparation of Peptides

S1 peptide (Ac-KKWRKWLAKK-NH$_2$, SEQ ID NO: 1) and S2 (Ac-KWWK-NH$_2$, SEQ ID NO: 2) ultra short peptide were purchased from peptide synthesis cooperations, and the N-terminal or C-terminal of S1 peptide was linked with β-Nal or tryptophan, separately, as shown in Table 1.

All of the peptides were synthesized by solid phase Fomc synthesis. HOBt/DIPEA as coupling agent and four fold molar excess of the Fmoc were added at every synthesis cycles. N-terminal amino protecting group of Fmoc was removed by 20% piperidine in DMF. 10-fold of acetic anhydride and 20-fold of DIPEA were dissolved in DMF at room temperature and then mixed for 2 hours to form the acetylated polypeptides. The polypeptides were isolated by columns, and the resin-bound peptides were eluted from the column by K reagent to obtain a cured extract of polypeptides. The cured extract of polypeptide was purified by HPLC to obtain a purified polypeptide, and then analyzed by FINNIGAN LCQ Mass Spectrometer.

TABLE 1

| Peptide | Sequence |
|---|---|
| S1 (SEQ ID NO: 1) | KKWRKWLAKK |
| Nal-S1 (SEQ ID NO: 3) | KK-Nal-RK-Nal-LAKK |
| S1-Nal (SEQ ID NO: 4) | KKWRKWLAKK-Nal |
| S1-Nal-Nal (SEQ ID NO: 5) | KKWRKWLAKK-Nal-Nal |
| S1-Nal-Nal-Nal (SEQ ID NO: 6) | KKWRKWLAKK-Nal-Nal-Nal |
| S1-W (SEQ ID NO: 7) | KKWRKWLAKKW |
| S1-W-W (SEQ ID NO: 8) | KKWRKWLAKKWW |
| S1-K-K-K (SEQ ID NO: 9) | KKWRKWLAKKKKK |
| S2 (SEQ ID NO: 2) | KWWK |
| S2-Nal (SEQ ID NO: 10) | KWWK-Nal |
| S2-F-Nal (SEQ ID NO: 11) | KWWK-F-Nal |
| S2-Nal-Nal (SEQ ID NO: 12) | KWWK-Nal-Nal |

Example 2: Salt Resistance Test

Antibacterial activity assay was used to determine the antimicrobial activity of S1, Nal-S1, S1-Nal-Nal, S1-Nal-Nal-Nal, S1-W, S1-W-W, S1-K-K-K, S2-Nal, S2-F-Nal, S2-Nal-Nal at different salt concentration. *Eschericha coli* (ATCC 25922), *Staphylococcus aureus* (ATCC 25923, 29213, and 19636), and *Pseudomonas aeruginosa* (ATCC 27853 and 9027) were used in the Example.

Microdilution method of National Committee for Clinical Laboratory Standards (NCCLS) was used to determine the minimal inhibition concentration (MIC). The MIC as used herein is a minimum inhibitory concentration required to inhibit the growth of 90% of organisms (MIC90).

In the Microdilution method, 1 μl of peptide solution (5,000 μg/ml to 78.1 μg/ml) and 99 μl of bacteria suspension were mixed and added into 96 wells plates. After 16 hours of incubation at 37° C., the optical density (O.D.) value at 600 nm was detected by ELISA (Thermo Max, Molecular Devices, Sunnyvale, Calif.). The Muller-Hinton Broth (MHB) medium without peptide and bacterial suspension were used as negative control and positive control, separately. The MIC value means a minimum inhibitory concentration required to inhibit the growth (equal or more than 90%) of bacteria. All experiments were repeated three times, and the results are shown in FIG. 1.

According to FIG. 1a, the antimicrobial activity of S1, Nal-S1, S1-W, S1-W-W, and S1-K-K-K was diminished at MHB medium or the high-salt condition. In comparison, S1-Nal, S1-Nal-Nal, and S1-Nal-Nal-Nal were better than S1, due to S1-Nal-Nal, and S1-Nal-Nal-Nal still retained the antimicrobial activities. Moreover, "Nal" improves the antimicrobial activity of the peptide either linked to N-terminal or C-terminal all.

Figure 1B:
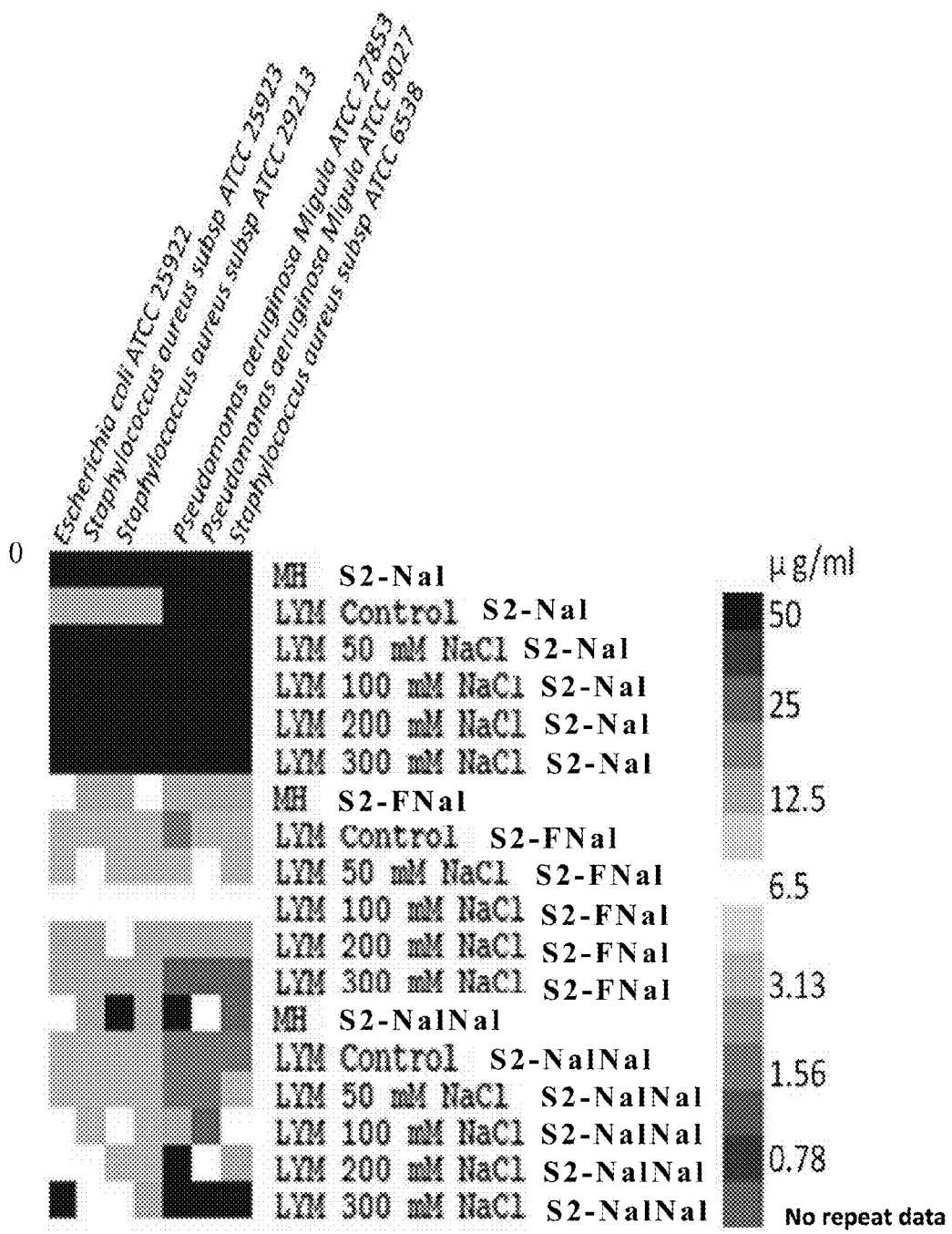
FIG. 1b shows the antimicrobial activity of the ultra short peptides.

According to FIG. 1b, the antimicrobial activity of S2-Nal, S2-F-Nal, and S2-Nal-Nal was diminished at MHB medium or the high-salt condition. In MHB medium or the high-salt condition, the antimicrobial activity of S2-F-Nal and S2-Nal-Nal was higher than that of S2-Nal. S2-F-Nal and S2-Nal-Nal were still retained their antimicrobial activities at 300 mM NaCl.

Additionally, the fluorescence quenching experiment demonstrated that β-Nal may help the peptides to pentrate deeper into the bacteria membrane, hence making them more efficient at disrupting the membrance.

Example 3: Hemolysis Assay

The hemolysis of peptides was determined by evaluating the effect of peptides on human red blood cells (hRBCs). hRBCs were obtained by washing the heparinized blood with PBS buffer three times, and stored at physiological saline with 10% phosphate buffer. The peptides were dissolved in PBS buffer, and then 50 µl of 10% (v/v) hRBCs was added to the PBS buffer at 37° C. for 1 hour of incubation (the final volume concentration of the hRBCs was 5%). After 1 hour of incubation, the hBRCs were centrifuged, and the hemolysis ratio was determined by detecting the absorbance values at 540 nm using a spectrophotometer. The hemolysis ratio of hRBCs without treatment was defined as 0%, and the hemolysis ratio of hRBCs treated with 1% Triton-X 100 was defined as 100%.

Figure 2A:
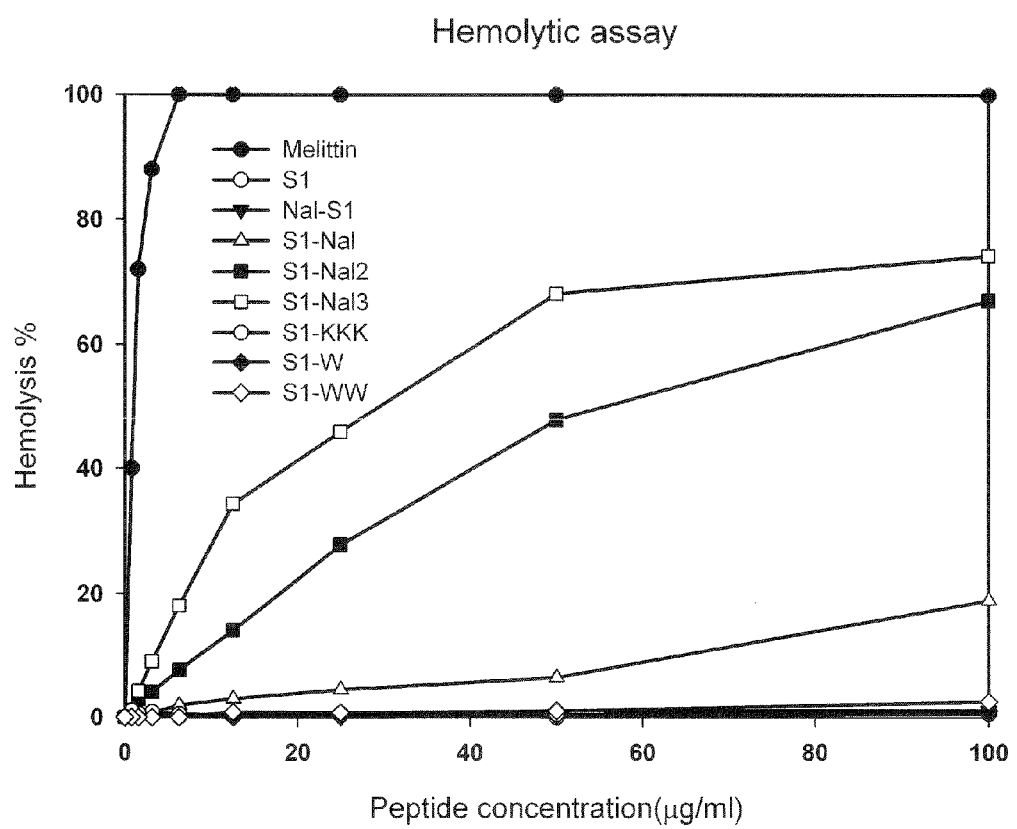
FIG. 2a shows the hemolysis of the peptides at different peptide concentrations.
Figure 2B:
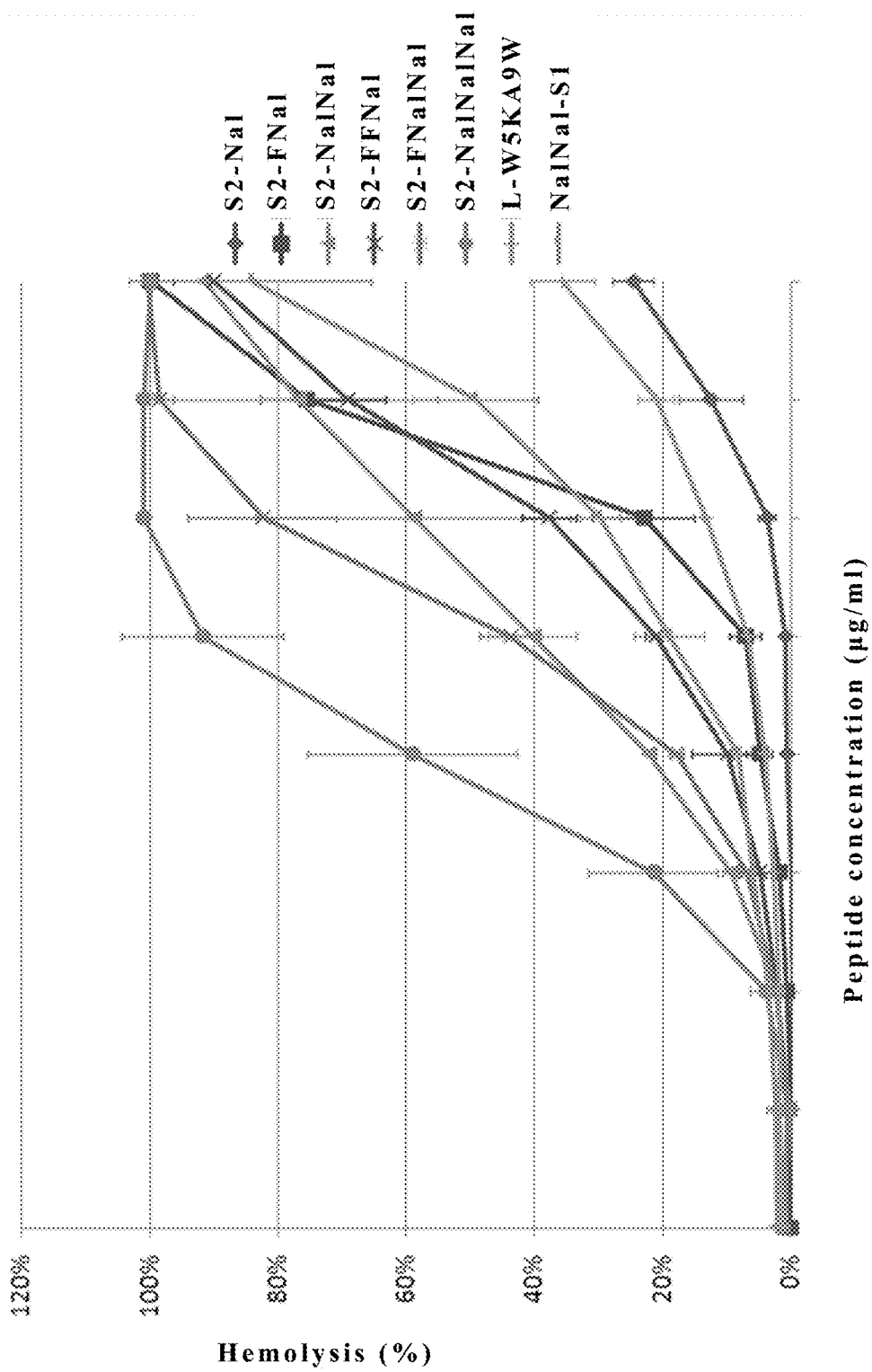
FIG. 2b shows the hemolysis of the ultra short peptides at different peptide concentrations.

According to FIGS. 2a and 2b, although S1-Nal-Nal and S1-Nal-Nal-Nal have a higher hemolytic activity than other peptides, all of the peptides exhibit the hemolytic activity of less than 5%.

Example 4: Protease Resistance

Serum stability of the peptides was determined in 25% (v/v) aqueous bovine calf serum (HyClone, cat. AUE-34962). Firstly, peptides were dissolved in serum at a concentration of 150 µg/mL and incubated at 37° C. After 45 min on ice for precipitating serum proteins, the serum was centrifuged at 12,000 g for 10 min at 4° C., and then the supernatants were lyophilized. Remaining amount of the peptides was determined by RP-HPLC.

Figure 3A:
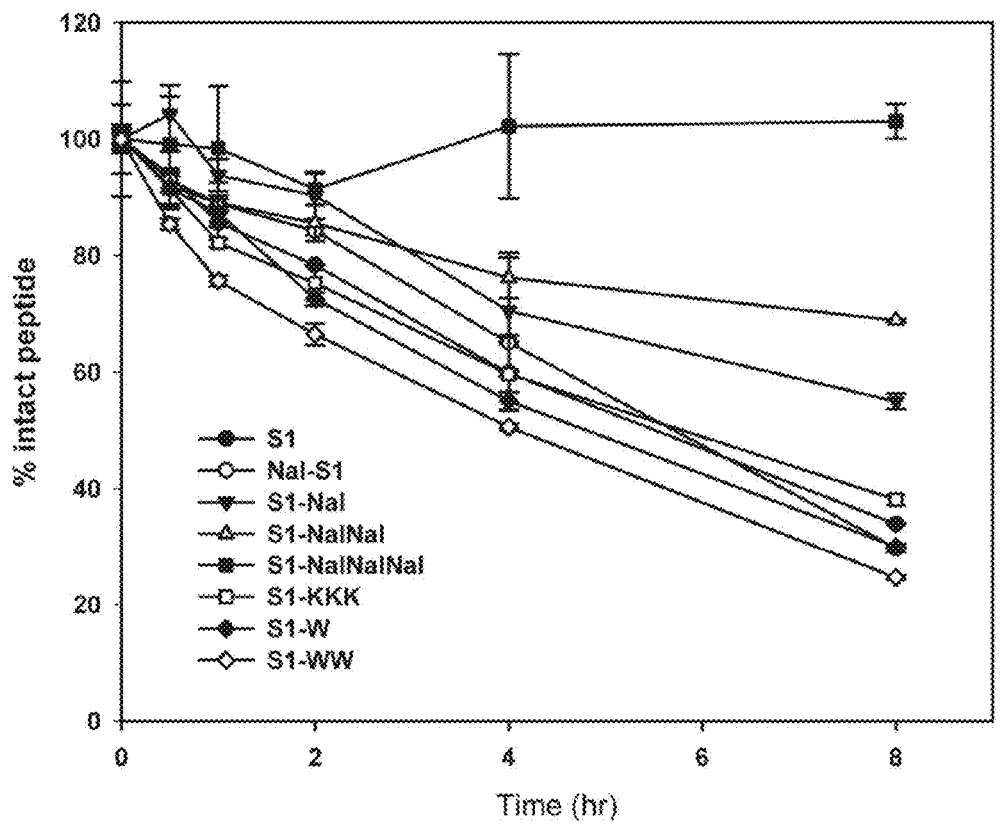
FIG. 3a shows the protease resistance of the peptides.
Figure 3B:
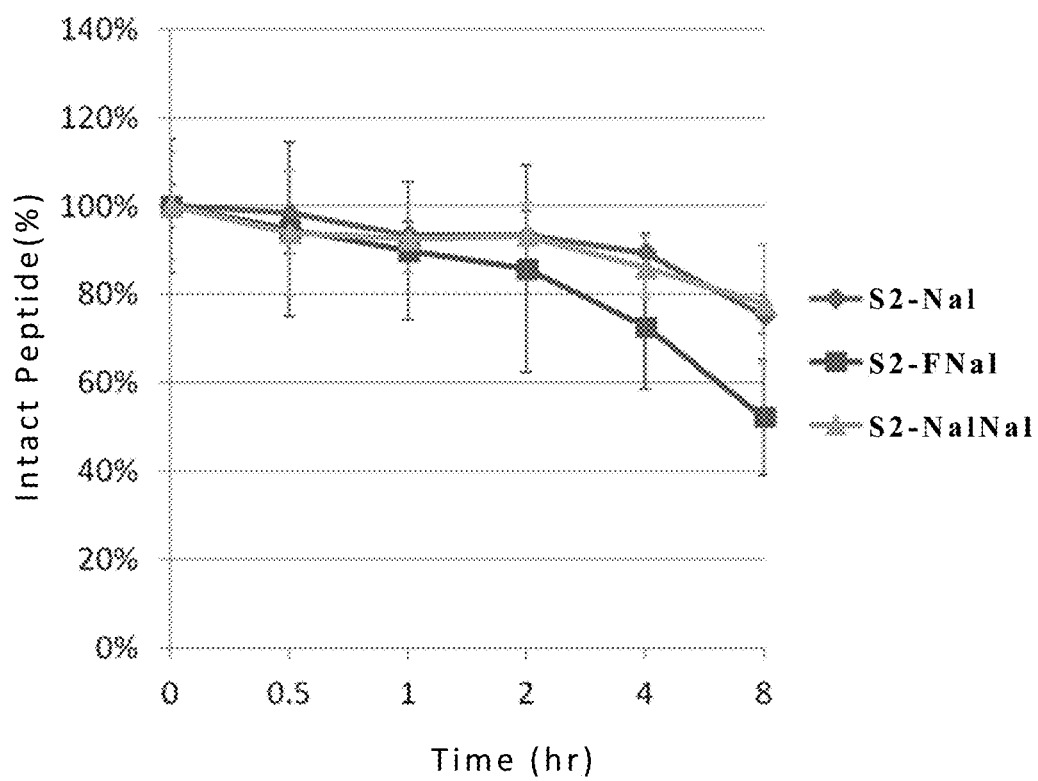
FIG. 3b shows the protease resistance of the ultra short peptides.

FIGS. 3a and 3b illustrate that β-Nal has an activity of protecting peptides in serum. According to FIG. 3, S1-Nal-Nal-Nal remained almost 100% of its integrity after 8 hours in bovin calf serum. The degree of protection of the peptides from degradation in bovine calf serum is S1-Nal-Nal-Nal>S2-Nal-Nal=S2-Nal>S1-Nal-Nal>S1-Nal>S2-F-Nal>S1-KKK>S1>Nal-S1=S1-W>S1-WW.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A peptide consisting of formula (I),

Lys-(Xp)-Bm, wherein p is from 2-8 and m is from 2 to 3, and p is a number of amino acid residues and m is a number of bulky amino acids;

wherein the peptide consisting of formula (I) has a length of 5-12 amino acids;

wherein X is selected from the group consisting of lysine, tryptophan, arginine, leucine, and alanine; and wherein B is selected from the group consisting of Nal, Dip, Bip, Ath, and Tbt.

2. The peptide as claimed in claim 1, wherein the (Xp) of the formula (I) comprises at least two positive-charged amino acids.

3. The peptide as claimed in claim 2, wherein the positive-charged amino acid is selected from the group consisting of lysine and arginine.

4. An antibiotic for suppressing microorganism infection comprising the peptide of claim 1 and a pharmaceutically acceptable adjuvant or carrier.

* * * * *